US012653973B2

(12) United States Patent
Hepting

(10) Patent No.: US 12,653,973 B2
(45) Date of Patent: Jun. 16, 2026

(54) EMERGENCY VENTILATOR WITH REMOVABLE COMMON COVER FOR SIMULTANEOUSLY COVERING FILTER AND BATTERY COMPARTMENT

(71) Applicant: Hamilton Medical AG, Bonaduz (CH)

(72) Inventor: Daniel Hepting, Maladers (CH)

(73) Assignee: Hamilton Medical AG, Bonaduz (CH)

( * ) Notice: Subject to any disclaimer, the term of this patent is extended or adjusted under 35 U.S.C. 154(b) by 750 days.

(21) Appl. No.: 18/014,281

(22) PCT Filed: Jul. 6, 2021

(86) PCT No.: PCT/EP2021/068623
§ 371 (c)(1),
(2) Date: Jan. 3, 2023

(87) PCT Pub. No.: WO2022/013004
PCT Pub. Date: Jan. 20, 2022

(65) Prior Publication Data
US 2023/0263976 A1 Aug. 24, 2023

(30) Foreign Application Priority Data
Jul. 13, 2020 (DE) ..................... 10 2020 118 467.0

(51) Int. Cl.
| *A61M 16/00* | (2006.01) |
| *A61M 16/10* | (2006.01) |
| *A61M 16/12* | (2006.01) |

(52) U.S. Cl.
CPC ....... *A61M 16/0066* (2013.01); *A61M 16/024* (2017.08); *A61M 16/107* (2014.02);
(Continued)

(58) Field of Classification Search
CPC .......... A61M 16/0057; A61M 16/0066; A61M 16/024; A61M 16/107; A61M 16/125;
(Continued)

(56) References Cited

U.S. PATENT DOCUMENTS

| 5,996,580 A | 12/1999 | Swann |
| 8,297,279 B2 | 10/2012 | Devries et al. |
| | (Continued) | |

FOREIGN PATENT DOCUMENTS

| CN | 106066066 A | 11/2016 |
| JP | H10192404 A | 7/1998 |

OTHER PUBLICATIONS

International Preliminary Report On Patentability for corresponding PCT/EP2021/068623 mailed Jan. 17, 2023, 6 pgs.
Japanese Office Action for corresponding 2023-501846 mailed Apr. 1, 2025, 5 pgs.
German Search Report for corresponding DE 10 2020 118 467.0 mailed Mar. 5, 2021, 6 pgs.
International Search Report for corresponding PCT/EP2021/068623 mailed Oct. 29, 2021, 12 pgs.

*Primary Examiner* — Joseph D. Boecker
(74) *Attorney, Agent, or Firm* — Rankin, Hill & Clark LLP

(57) ABSTRACT

An emergency ventilator for artificially ventilating patients in the event of a medical emergency, including: —a housing with an ambient air suction opening and a ventilating gas outlet opening, —a fan which is designed and is arranged in the housing so as to convey ambient air from the ambient air suction opening to the ventilating gas outlet opening, —an air filter which is designed to purify suctioned ambient air and which is arranged in the housing downstream of the ambient air suction opening in the flow path of the ambient air, and —an energy storage device for supplying the fan with energy in order to operate same, wherein the air filter is received in the housing in an accessible manner through a housing opening, which is closed but can be opened by a housing cover, and so as to be replaceable in an intended manner, and the energy storage device is received in the
(Continued)

housing in an accessible manner through the housing opening, which is closed but can be opened by the housing cover, and so as to be replaceable in an intended manner, the air filter and the energy storage device can be accessed through a common housing opening, the common housing opening being selectively closable and openable by a common housing cover.

18 Claims, 6 Drawing Sheets

(52) U.S. Cl.
CPC ..... *A61M 16/125* (2014.02); *A61M 2205/125* (2013.01); *A61M 2205/505* (2013.01); *A61M 2205/8206* (2013.01)

(58) Field of Classification Search
CPC ...... A61M 2205/125; A61M 2205/505; A61M 2205/8206
See application file for complete search history.

(56) References Cited

U.S. PATENT DOCUMENTS

| | | | | |
|---|---|---|---|---|
| 10,870,076 | B1 * | 12/2020 | Lynch | B01D 46/0036 |
| 2007/0169776 | A1 * | 7/2007 | Kepler | C07K 7/56 |
| | | | | 128/200.14 |
| 2011/0197882 | A1 * | 8/2011 | Truschel | A61M 16/0057 |
| | | | | 429/99 |
| 2015/0083121 | A1 | 3/2015 | Fisher et al. | |
| 2015/0190605 | A1 | 7/2015 | Martin et al. | |
| 2016/0114121 | A1 | 4/2016 | Holley et al. | |
| 2018/0028846 | A1 | 2/2018 | Hur et al. | |
| 2019/0117919 | A1 * | 4/2019 | Panarello | H02J 9/061 |
| 2019/0366025 | A1 | 12/2019 | Diehl et al. | |

OTHER PUBLICATIONS

Chinese Office Action for corresponding 202180046387.2 mailed Jun. 10, 2025, 9 pgs.
Espacenet Bibliographic data: CN 106066066 (A), Published Nov. 2, 2016, 1 pg.

* cited by examiner

EMERGENCY VENTILATOR WITH REMOVABLE COMMON COVER FOR SIMULTANEOUSLY COVERING FILTER AND BATTERY COMPARTMENT

This application claims priority in PCT application PCT/EP2021/068623 filed on Jul. 6, 2021, which claims priority in German Patent Application DE 10 2020 118 467.0 filed on Jul. 13, 2020, which are incorporated by reference herein.

The present invention concerns an emergency ventilator for emergency medicine artificial respiration of patients, comprising A housing with an ambient air aspiration aperture and a respiratory gas output aperture, A fan which is configured and arranged in the housing in order to convey ambient air from the ambient air aspiration aperture to the respiratory gas output aperture, An air filter which is configured for cleaning aspirated ambient air and is arranged in the housing in the flow path of the ambient air downstream from the ambient air aspiration aperture, and An energy store for supplying the fan with energy for its operation, Where the air filter is accessible through a housing aperture which is closed by means of a housing lid but is openable and in normal operation is accommodated in the housing in a replaceable manner, and Where the energy store is accessible through a housing aperture which is closed by means of a housing lid but is openable, and in normal operation is accommodated in the housing in a replaceable manner.

BACKGROUND OF THE INVENTION

As such an emergency ventilator there are known the ventilator with the designation 'EVE$_{IN}$' of Fritz Stephan GmbH in Gackenbach (DE) and the ventilator with the designation 'Falco 202 Evo' of the Italian firm Siare Engineering International Group s. r. l. in Valsamoggia (IT).

Emergency ventilators, inter alia also referred to as 'intensive care ventilators', serve for rapid supply of respiratory gas to a patient outside a clinical environment, i.e. for instance at an accident site and/or during transportation of a patient. Of course, emergency ventilators can also be used in a clinical environment, however in hospitals often more powerful ventilators are available as emergency ventilators.

As ventilators which are deployable outside a clinical environment, emergency ventilators exhibit their own energy store which at least for a certain duration allow operation of the emergency ventilator independently of a power grid supply. Furthermore, emergency ventilators are designed as portable ventilators with regards to their size and weight, such that they can be moved by emergency medical personnel, for instance an emergency physician called to an accident location, with just their own muscle strength even over distances of several hundred meters without excessive physical stress.

Without supplementary special gas reservoirs, such as for instance an oxygen reservoir, emergency ventilators are designed due to their fan to be able to provide at least ambient air as respiratory gas. To the ambient air there can be added when needed a special gas different from the ambient air, in the most frequent case pure oxygen but also anesthetic and/or therapeutic gases and gas mixtures. To this end, emergency ventilators usually exhibit a connector formation for connecting a special gas reservoir.

Ambient air, which is aspirated by the emergency ventilator as respiratory gas, can be contaminated. Consider here, for example, accident victims that have to receive emergency medical treatment on building sites or in another dusty or sandy environment.

In order to be able to provide adequately clean respiratory gas to a patient who has to be artificially ventilated on site, there is arranged in the flow path of the ambient air from the aspiration aperture up to the patient air filter, which depending on its filter properties removes dirt from the aspirated ambient air, such that the dirt does not reach the patient. The air filter is arranged in the housing of the emergency ventilator between the ambient air aspiration aperture and the respiratory gas output aperture.

Both the air filter and the energy store have a finite lifespan which is considerably shorter than the service life of the emergency ventilator. Accordingly, they have to be frequently replaced. For emergency ventilators it is essential that they can be made operational in the shortest possible time. During a replacement of the air filter or of the energy store, the emergency ventilator not operational.

SUMMARY OF THE INVENTION

It is, therefore, the task of the present invention to develop the aforementioned emergency ventilator in such a way that in the event of a necessary replacement of the air filter and/or of the energy store, it becomes inoperative for the shortest possible time.

The present invention solves this task in an emergency ventilator with the features named at the beginning by having the air filter and the energy store accessible through a common housing aperture, where the common housing aperture can be closed and opened selectively through a common housing lid.

Unlike the aforementioned emergency ventilators, which exhibit the air filter and the energy store at different locations in the respective housing, such that the air filter and the energy store are accessible through different housing apertures, where the different housing apertures can be closed through separate housing lids, in the present emergency ventilator the air filter and the energy store are accessible through one and the same common housing aperture, where the common housing aperture can be closed through a single common housing lid.

This allows it to suffice, when both the air filter and the energy store have to be replaced, to remove only a single common housing lid in order to make both air filter and energy store accessible and be capable of replacing. Likewise, after the replacement only a single common housing lid has to be arranged again at the common housing aperture. That always both components are accessible when only one component out of air filter and energy store has to be replaced is not only harmless, since already the replacement of one of these components renders the emergency ventilator inoperative, but even advantageous. This is because through the fact that only a common housing lid has to be removed, a time-consuming, undesirable mixing up of different housing lids assigned to different components is impossible, such that through the use of the common housing lid over many replacement procedures the mean downtime of the emergency ventilator is also shortened.

The energy store is normally an electrical energy store, such as a battery or a rechargeable storage battery or in short 'storage battery'.

A state denoted below as 'locking state' of the emergency ventilator denotes a state in which the common housing lid closes, i.e. covers, the common housing aperture, such that components and component sections arranged from outside behind the housing aperture are shielded by the common housing lid and consequently are not accessible.

In order to prevent unintentional removal of the common housing lid from the common housing aperture, the common housing lid is preferably latchable to the remaining rest of the housing which exhibits the housing aperture. For secure latching, the common housing lid preferably exhibits a latching formation which can be brought into positive-locking engagement with a housing-tight latching counter-formation. A positive-locking engagement makes, by means of physical blocking of movement of the common housing lid relative to the common housing aperture effected by it, for especially secure latching of the common housing lid to the common housing aperture.

The attribute 'common' is omitted below in the formations 'housing lid' and 'housing aperture', since every further mention of the housing lid and of the housing aperture denotes the common housing lid or the common housing aperture, as the case may be.

The remaining housing without the housing lid removed from it is also referred to below as 'rest of the housing'.

'Housing-tight' here does not necessarily mean configured directly at the housing, although this is also comprised by the term 'housing-tight'. 'Housing-tight' means 'in normal operation, not separable and/or not removable respectively from the housing and/or the rest of the housing respectively except for any repair purposes'.

A formation out of latching formation and latching counter-formation can be a projection, which can protrude into the respective other formation out of latching formation and latching counter-formation which is then configured as a recess, forming a positive-locking engagement.

In principle the latching formation can be arranged rigidly at the housing lid and the latching counter-formation can be arranged moveably between a latching position and a releasing position at the rest of the housing. In the latching position the latching formation is in positive-locking engagement with the latching counter-formation, in the releasing position in contrast not. In order to make it possible, however, in an advantageous development of the present invention, to take the housing lid off the rest of the housing with one hand and even more preferably with a single fluid movement, preferably the latching formation is provided on the housing lid moveably between a latching position and a releasing position. An actuating formation to be gripped by hand for actuating the latching formation between the latching position and the releasing position is also preferably provided on the housing lid.

With regard to the most secure and tight closure possible of the housing aperture through the housing lid with at the same time possible one-handed operation of the housing lid for its removal from the housing aperture and for its arrangement at the housing aperture as well as its latching there, it is preferably provided that the housing lid exhibits a lid component which in the locking state of the emergency ventilator is immoveable relative to the remaining housing and a latching component which is moveable relative to the remaining housing. The latching component carries the aforementioned latching formation, and preferably likewise the aforementioned actuating formation, and is preferably moveable between the latching position, in which the latching formation of the latching component, through positive-locking engagement with the housing-tight latching counter-formation on the remaining ventilator, latches the housing lid against removal from the housing aperture and the releasing position, in which the latching component allows removal of the housing lid from the housing aperture.

In order to keep the number of components needed for providing the housing lid as small as possible, the latching component is preferably arranged and fastened at the lid component moveably relative to the lid component.

In principle, the latching component can be translationally moveable relative to the lid component between the latching position the releasing position. Since, however, normally the housing lid is removed translationally from the housing aperture, it is advantageous for one-handed operation of the housing lid with at the same time the greatest possible operating safety against an undesirable operating error if the latching component is mounted on the lid component rotatably about a latching axis relative to the lid component. The housing lid can preferably be lifted off the housing aperture along the latching axis. Then the housing lid closing the housing aperture and latched can be unlatched through rotation of the latching component about the latching axis and removed from the housing aperture along the latching axis without changing the manual grip on the latching component.

In principle, the latching formation and the latching counter-formation can each be a thread, which in the latching position are in screw engagement with one another and in the releasing position not. Admittedly, a screw engagement offers especially secure latching. However, its release and its restoration require not inconsiderable time. Preferably, therefore, the latching formation and the latching counter-formation form a bayonet catch. A formation out of latching formation and latching counter-formation, therefore, exhibits at least one projection which is radial in respect of the latching axis and the respective other formation exhibits a recess which accommodates the projection with a section which is axial in respect of the latching axis and at least one circumferential edge proceeding in the circumferential direction about the latching axis and engaged from behind in the latching position by the projection. The edge can be a flank of a circumferential section of the recess. When the housing lid approaches the housing aperture along the latching axis, the projection in the axial section can slide axially relative to the recess until the circumferential edge has passed the projection axially. Then the projection can, in order to shift into the latching position through rotation of the latching component about the latching axis, slide along the circumferential edge where it engages physically behind the latter. A movement of the housing lid in the axial direction away from the housing aperture is thereby prevented in a positive-locking manner.

Since the housing lid creates access to the air filter which is arranged in the flow path of the ambient air from the ambient air aspiration aperture to the respiratory gas outlet aperture, in order to achieve an advantageously compact construction of the emergency ventilator the housing lid preferably comprises the ambient air aspiration aperture. Thereby it is moreover possible to arrange the air filter near the housing lid, preferably directly behind it, upstream of the fan, such that only cleaned air flows through the fan. This increases the service life of the fan.

In principle, the ambient air aspiration aperture can be arranged in the lid component. For the most secure actuation possible of the latching component even in very poor light conditions, it is preferably configured as relatively large, such that it is also locatable easily and quickly by touch. Therefore the ambient air aspiration aperture can readily penetrate through the latching component.

When the ambient air aspiration aperture penetrates through the latching component, preferably the latching axis penetrates through the ambient air aspiration aperture, such that during a rotation of the latching component about the latching axis the position of the ambient air aspiration aperture relative to the rest of the housing changes as little as possible. For this reason, the ambient air aspiration aperture is especially preferably arranged centrically at the latching component and is penetrated through centrically by the latching axis. In the event of a preferentially circular ambient air aspiration aperture, its position does not change during a rotation of the latching component about the latching axis such that the emergency ventilator continues to be ready for use even during the unlatching of the housing lid.

According to a structurally preferred embodiment, for rotatable mounting of the latching component the lid component can exhibit a mounting section surrounding the ambient air aspiration aperture which is coaxial to the latching axis and which is surrounded by a mounting counter-section of the latching component which extends along the latching axis and is coaxial to the latching axis. Then the mounting section as a kind of axial component can carry the latching component rotatably about the latching axis. To achieve an advantageously large mounting length, the mounting section can protrude from the remaining lid component along the latching axis.

In order to be able to arrange at the emergency ventilator additional filters for cleaning the aspirated ambient air and/or a measuring instrument for acquiring physical and/or chemical properties of the aspirated ambient air, such as for instance temperature, contamination with predetermined suspended matter or ingredients, or composition, the mounting section exhibits on its relative to the latching axis radial inner side which faces away from the mounting counter-section an attachment formation, preferably a thread, in particular inner thread, or part of a further bayonet catch, to which attachment formation the additional filters and/or the measuring instrument can be attached.

Preferably the housing lid serves not only for closing the housing aperture, but rather it also contributes to the positional fixing of functional components which in the locking state are accommodated in the housing behind the housing lid. Therefore according to a preferred development, the housing lid exhibits a lid-filter positioning section which in the locking state faces towards the interior of the housing and which in the locking state with an operational emergency ventilator, acting together with at least one housing-tight housing-filter positioning section, secures a filter cartridge for filtering ambient air in its operational position.

Additionally or alternatively, the common housing lid can exhibit a lid-store positioning section which in the locking state faces towards the interior of the housing and which in the locking state with an operational emergency ventilator, acting together with at least one housing-tight housing-store positioning section, secures an energy store body in its operational position. The energy store body can be the aforementioned battery or the rechargeable storage battery.

In the locking state, the mentioned housing-side positioning sections and the assigned lid-side positioning sections are preferably in abutting engagement with the respective positioned component: filter cartridge and energy store body, where a positive-locking engagement between a positioning section and the positioned component should also not be excluded.

The filter cartridge preferably exhibits a filter housing and a filter, in particular HEPA filter, accommodated in the filter housing where in the event of an opened housing aperture, the filter cartridge as a component can be withdrawn from the rest of the housing and inserted in the rest of the housing, respectively. Likewise the energy store body is preferably a single energy store body, although it should not be excluded that a higher energy demand of an emergency ventilator requires more than one energy store body.

The filter cartridge exhibits an ambient air inlet aperture which in the operational state of the emergency ventilator can be reached through the ambient air aspiration aperture. To prevent the ingress of large dirt particles, it can be provided with a protective grille. The protective grille can, for instance in the event of injection-molded configuration of the filter cartridge, be configured integrally with a component of the cartridge housing. Since, as already suggested above, in some ventilation situations it can be required, in addition to the ambient air, to administer a special gas which differs from it, the filter cartridge can in addition to the ambient air inlet aperture exhibit a special gas connector formation for connecting a special gas supply.

So that the special gas connector formation of the filter cartridge can be reached easily through the ambient air aspiration aperture of the housing lid, it is advantageous if the special gas connector formation is arranged at a radial distance—in relation to a virtual axis conceived as penetrating centrally through the ambient air aspiration aperture—from an edge of the ambient air aspiration aperture. Preferably, therefore, the ambient air inlet aperture and the special gas connector formation are arranged coaxially to one another. Especially preferably, in the operational locking state the special gas connector formation is also arranged coaxially to the latching axis.

Numerous state-of-the-art emergency ventilators display a complex outer shape with numerous surfaces bent relative to one another. Such a shape can be awkward in the agitation and rush of an emergency deployment, since hoses and wires can get entangled at corners and in gaps in such complex shapes. Preferably, therefore, the housing of the present emergency ventilator has a simple housing shape, preferably with a prismatic and/or cylindrical basic form. Consequently the housing preferably has two end faces essentially parallel to one another and a lateral surface connecting the two end faces with one another. The lateral surface encircles a virtual prism axis connecting the end faces with one another. The lateral surface can be configured in polyhedral shape with consecutive planar surfaces in the circumferential direction about the prism axis. To prevent injuries, the connecting regions between two directly adjacent planar lateral surface sections in the circumferential direction are rounded. The radius of curvature of such a connecting section preferably exhibits at least 0.5 cm. The axis of curvature is preferably parallel to the prism axis. The lateral surface can likewise be configured as a cylindrical, where the cross-sectional area of the cylindrical basic form can be circular or elliptical.

The lateral surface can also be both prismatic and cylindrical, if for instance it is configured along a first circumferential section as polyhedral and along a second circumferential section adjoining the former as cylindrical or part-cylindrical, as the case may be.

The housing component exhibiting the lateral surface is preferably a tubular housing component, where its tube axis is the prism axis. For reasons of low weight and good heat conduction, the tubular housing component is preferably made from a light metal such as an aluminum or magnesium alloy, can additionally or alternatively also be made from a copper alloy such as for example brass or bronze, or also from a copper-containing alloy. In deviation thereof, the tubular housing component can be fabricated from a synthetic, in particular from a thermoplastic synthetic. To increase the heat conductance, the synthetic can be filled with particles which increase the heat conductance of the mixture compared with the unfilled synthetic matrix. Such a filling material is for example boron nitride.

For reasons of increased stability, the tubular housing component is preferably fabricated joint-free, for instance as an extrusion-pressed component or as an extrusion-molded component.

The housing lid preferably forms an end face of the prismatic and/or cylindrical housing. Thus the lateral surface of the housing can be used for the arrangement of the housing lid at the rest of the housing. Of course, alternatively the housing aperture can also be created in an existing housing wall by cutting out wall material. This expense, however, is not necessary if one uses a housing aperture which is formed anyway during the production of a housing with a prismatic and/or cylindrical basic form, such as for instance an end-face aperture.

For better orientation of a person operating the emergency ventilator even in poor light conditions, it is advantageous if all connector formations and/or apertures which introduce a gas into the housing and channel gas out of the housing are arranged cumulatively at only one end face or distributed at both end faces of the prismatic and/or cylindrical housing. Besides, connecting formations which protrude and therefore at risk of being damaged, such as for instance connector nozzles, can thus be avoided at the lateral surface. Possible connecting formations can be nozzles, in particular threaded nozzles, quick couplings, threaded recesses, and the like.

For operating and controlling the emergency ventilator it preferably exhibits an input/output device with which data and/or control commands can be input into the emergency ventilator and with which data about the operation of the emergency ventilator can be displayed to the operator. The input/output device therefore preferably exhibits a display device, such as for instance a screen, and exhibits at least one switching device, such as for example a pushbutton switch and/or a toggle switch and/or a rotary switch. The screen can preferably be a touchscreen, such that the quantity of pushbuttons, i.e. pushbutton switches, firmly installed on the emergency ventilator can be kept low. The input/output device and also the further control and evaluation electronics of the emergency ventilator are likewise supplied with energy by the energy store.

More preferably, the prismatic and/or cylindrical housing exhibits the input/output device with the display device and the at least one switching device in the region of its lateral surface, preferably only in the region of its lateral surface.

Preferably most, i.e. more than half, preferably more than 70%, of the housing wall observable from outside is fabricated from impact-resistant material, such as for instance from metal or from a synthetic, in particular filled synthetic, in order to fit out the emergency ventilator sufficiently robustly for the often rough environment and handling in emergency deployments. For reasons of weight, a metal housing wall is preferably made from an aluminum or magnesium alloy. In order, nevertheless, not to transmit shocks, which perhaps can arise when the emergency ventilator is put down forcefully, undamped to the electronics in the interior of the emergency ventilator, the emergency ventilator preferably exhibits on its outer surface at least one shock-absorbing element.

The shock-absorbing element is preferably made from an elastomeric synthetic, such as for instance natural or synthetic rubber, in particular silicone rubber, which has a considerably lower modulus of elasticity than the robust material which forms most of the housing wall. Because of the advantageous possibilities for primary shaping, a thermoplastic elastomer is an advantageous elastomeric synthetic. The at least one shock-absorbing element is preferably arranged on the outer surface of the housing lid. In the case of the preferred configuration of the housing lid as a complete end face of a prismatic and/or cylindrical housing, the at least one shock-absorbing element is preferably provided in the circumferential direction around the prism axis at the housing lid, especially preferably encircling the prism axis completely in a closed manner.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which forms a part hereof and wherein.

DESCRIPTION OF PREFERRED EMBODIMENTS

Figure 1:
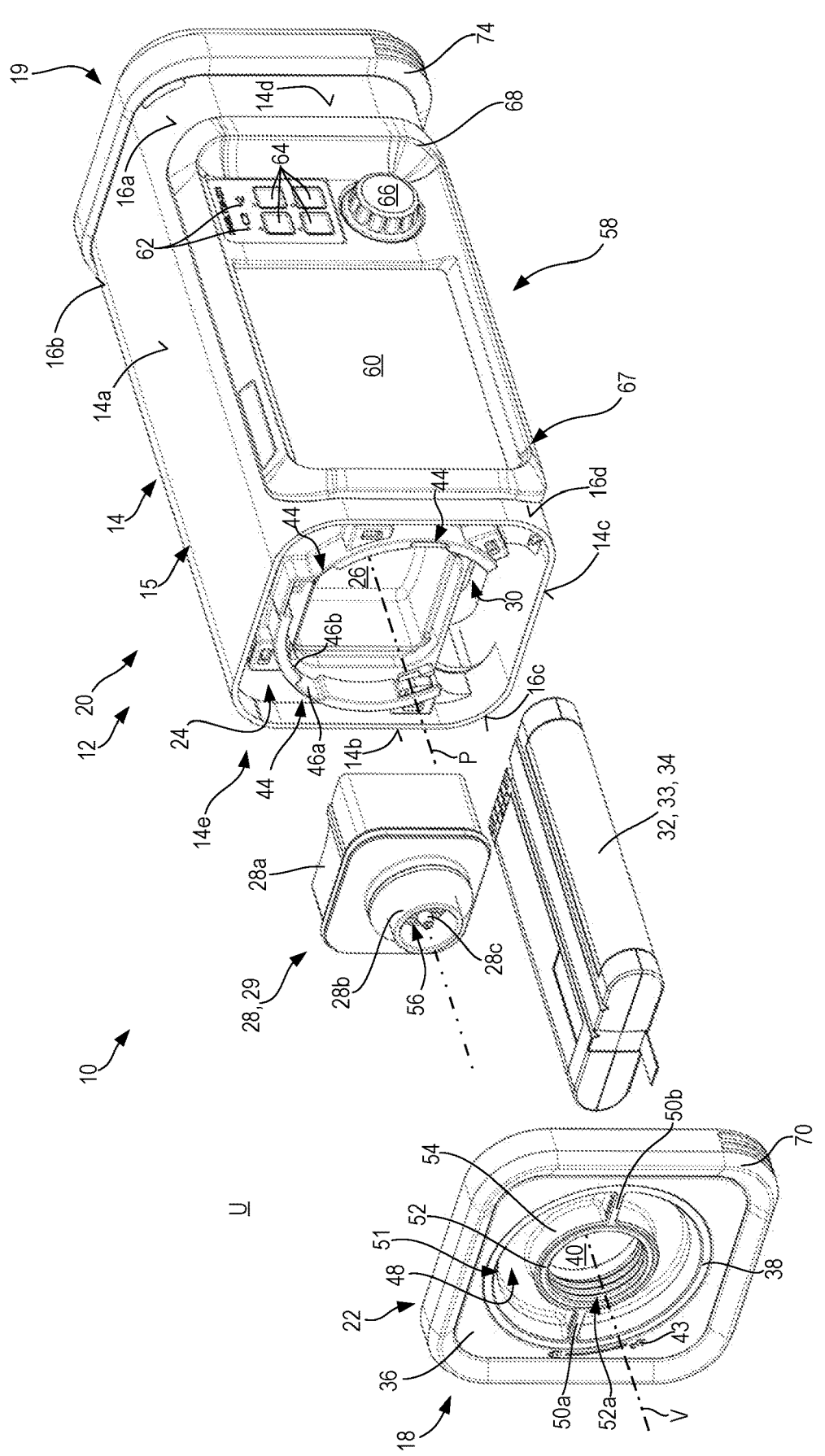
FIG. 1A perspective exploded view of an emergency ventilator according to the invention, FIG. 2A longitudinal section through the emergency ventilator according to the invention of FIG. 1, with a sectional plane parallel to the surfaces 14*b* and 14*d* in FIG. 1, FIG. 3A plan view of the one end face formed by a removable housing lid of the emergency ventilator of FIGS. 1 and 2, FIG. 4A plan view of the other, opposite end face of the emergency ventilator of FIGS. 1 and 2, FIG. 5A longitudinal section view along the sectional plane V-V of FIG. 7, FIG. 6A cross-section view along the sectional plane VI-VI of FIG. 7 which is orthogonal to the prism axis P, and FIG. 7A plan view of the planar front face 14*d* with the input/output device 58 of the emergency ventilator of FIG. 1.

Referring now to the drawings wherein the showings are for the purpose of illustrating preferred and alternative embodiments of the invention only and not for the purpose of limiting the same, in FIG. 1, an embodiment according to the invention of an emergency ventilator is labelled generally by 10. The emergency ventilator 10 comprises a housing 12 with a prismatic basic form, in the present case with a cuboidal basic form.

The lateral surface 14 of the housing 12 comprises four planar area segments 14*a*, 14*b*, 14*c*, and 14*d*, of which planar area segments 14*a*, 14*b*, 14*c*, and 14*d* respectively following one another in the circumferential direction about the prism axis P are oriented orthogonally to one another. All planar area segments 14*a*, 14*b*, 14*c*, and 14*d* are parallel to the prism axis P. The planar area segments 14*a*, 14*b*, 14*c*, and 14*d* are connected with one another preferably without joints through quarter-cylindrical area segments 16*a*, 16*b*, 16*c*, and 16*d*. The individual cylinder axes of the quarter-cylindrical and thereby curved area segments 16*a*, 16*b*, 16*c*, and 16*d* are parallel to the prism axis P. The housing component 15 exhibiting the lateral surface 14 is preferably an extruded aluminum tube.

On the end face 18 of the housing 12 facing towards the observer of FIG. 1 the housing 12 comprises a housing lid 22 which is removable from the rest of the housing 20 along the prism axis P and which can be arranged at the rest of the housing 20. The housing lid 22 consequently serves for capping a housing aperture 24 formed at the longitudinal end 14*e* lying nearer to the observer of FIG. 1 of the lateral surface 14. The housing aperture 24 is bounded by the lateral surface 14 of the rest of the housing 20. Through the housing aperture 24 there is accessible a filter accommodating compartment 26 for an air filter cartridge 28 with an air filter 29 and there is accessible a storage battery accommodating compartment 30 for a rechargeable electric storage battery 32 as a power-grid independent energy store 34.

The housing lid 22 exhibits a lid component 36 and a latching component 38. The latching component 38 is mounted at the lid component 36 rotatably about the latching axis V. In the locking state, i.e. when the housing lid 22 is arranged at the rest of the housing 20 and closes the housing aperture 24, the latching axis V proceeds coaxially with the prism axis P.

The housing lid 22 exhibits furthermore an ambient air aspiration aperture 40, which penetrates through both the lid component 36 and the latching component 38. Through the ambient air aspiration aperture 40, ambient air can be aspirated by a fan 42 (see FIG. 2) from the environment U through the air filter 29 into the housing 12.

The latching component 38 is shown in FIG. 1 in its latching position, from which it is rotatable anti-clockwise for instance by a twelfth of a rotation about the latching axis V into a releasing position denoted by a symbol 43 in the shape of an open padlock. The latching component 38 exhibits projections, which in FIG. 1 are hidden by the lid component 36, protruding radially in the direction away from the latching axis V. These projections are part of a bayonet catch, through which the housing lid 22 which closes the housing aperture 24 can be latched in a positive-locking manner to a latching counter-formation 44 which is immovable relative to the rest of the housing 20. The latching counter-formation 44 exhibits for this purpose several recesses 46, each with an axial recess section 46*a* and with a recess section 46*b* in the circumferential direction about the latching axis V. The projections of the latching component 38 can, when it is in the releasing position, be guided along the axial recess section 46*a* parallel to the latching axis V and thereby parallel to the prism axis P to the recess section 46*b* and after reaching the recess section 46*b* be moved in the circumferential direction along the recess section 46*b*.

The latching component 38 exhibits a recessed handle 48 proceeding in the circumferential direction, which is interrupted by two gripping bars 50*a* and 50*b* which lie diametrically opposite one another relative to the ambient air aspiration aperture 40 located between them. By manually gripping the gripping bars 50*a* and 50*b*, the latching component 38 can be rotated between the releasing position and the latching position and also the released housing lid 22 can be lifted off along the prism axis P from the rest of the housing 20 or attached onto the latter. The gripping bars 50*a* and 50*b* and the recessed handle 48 form together an actuating formation 51 for actuating the latching component 38.

Through one-handed operation, therefore, the housing lid 22 is removable from the rest of the housing 20 and also attachable to the latter and also in the closed position latchable and releasable.

The ambient air aspiration aperture 40 is directly bordered radially outwards-relative to the latching axis V—by a mounting section 52 of the lid component 36. The mounting section 52 exhibits an attachment formation 52*a* in the form of an inner thread. At this attachment formation 52*a* there can be arranged for example an additional air filter which fulfils filtering functions which the air filter 29 of the air filter cartridge 28 does not perform. Alternatively or additionally, there can be arranged at the attachment formation 52*a* a measuring device which records metrologically the aspirated ambient air flowing through the ambient air aspiration aperture 40, for instance determines its chemical composition or determines whether and where applicable to what extent the aspirated ambient air does or does not contain a predetermined constituent.

The mounting section 52 is surrounded radially outward by a mounting counter-section 54 of the latching component 38. The mounting section 52 acts so to speak as an axis component, which mounts the latching component 38 by means of its mounting counter-section 54 rotatably about the latching axis V. The mounting counter-section 54 forms a radial inner limit of the recessed handle 48.

The air filter cartridge 28 exhibits on its side which during operation faces towards the housing lid 22 an ambient air inlet aperture 56 which is bordered by a collar 28*b* protruding out from the cartridge main body 28*a*. In the operational state of the emergency ventilator 10, a cartridge inlet axis K which is conceived as penetrating centrally through the collar 28*b* is coaxial to the latching axis V and to the virtual prism axis P which is conceived as penetrating centrally through the lateral surface 14. The ambient air inlet aperture 56 is protected by a protective grille 57 (see FIG. 3) against ingress of larger dirt particles such a stones, dust balls and the like. The protective grille 57 can be configured by injection molding integrally with a housing part of the air filter cartridge 28 which exhibits the ambient air inlet aperture.

Concentrically to the collar 28*b* there projects along the cartridge inlet axis K a special gas auxiliary inlet 28*c* in the shape of a protruding connection nozzle which tapers away from the cartridge main body 28*a*. A special gas supply, for example an oxygen auxiliary supply, can be connected to the special gas auxiliary inlet 28*c* rapidly and in an uncomplicated manner, for example by an elastic hose which is sufficiently small or large as the case may be in its diameter being pushed onto the special gas auxiliary inlet 28*c* and held there in a frictionally engaged manner. Through the shape of the special gas auxiliary inlet 28*c* which tapers away from the cartridge main body 28*a*, hoses in a predetermined diameter range can be connected with the special gas auxiliary inlet 28*c* sufficiently securely on short notice.

The energy store 34 exhibits in the depicted preferred embodiment example a single energy store body 33.

On the planar area segment 14*d* and starting off from it extending into the part-cylindrical neighboring area segments 16*d* and 16*a*, the emergency ventilator 10 exhibits an input/output device 58 which serves for the information exchange between the operator and the emergency ventilator 10 and which serves for the control of the emergency ventilator 10 by the operator. The input/output device 58 exhibits a screen 60 as an output device, which preferably is a touchscreen, which in a touch-sensitive manner allows the input of information. The input/output device 58 moreover exhibits display LEDs 62 as further output device and exhibits by way of example pushbuttons 64 and a rotary switch 66 as input means.

As protection from impact-like stresses, the input/output device 58 can be surrounded by a framing component 67, in an exemplifying configuration as a shock-absorbing elastomer ring 68, for instance made from synthetic rubber, natural rubber, and the like. The framing component 67 surrounding the input/output device 58 can, however, also be formed as a synthetic injection-molded component from a thermoplastic synthetic.

The appliance lid 22 too, is surrounded by a shock-absorbing elastomer ring 70 encircling completely in circumferential direction about the prism axis P. In the locking state the elastomer ring 70 covers part of the lateral surface 14 just as it does of the end face 18, such that the elastomer ring 70 protects the emergency ventilator 10 in the region of the appliance lid 22 both against axial and against radial impact stresses.

Figure 2:
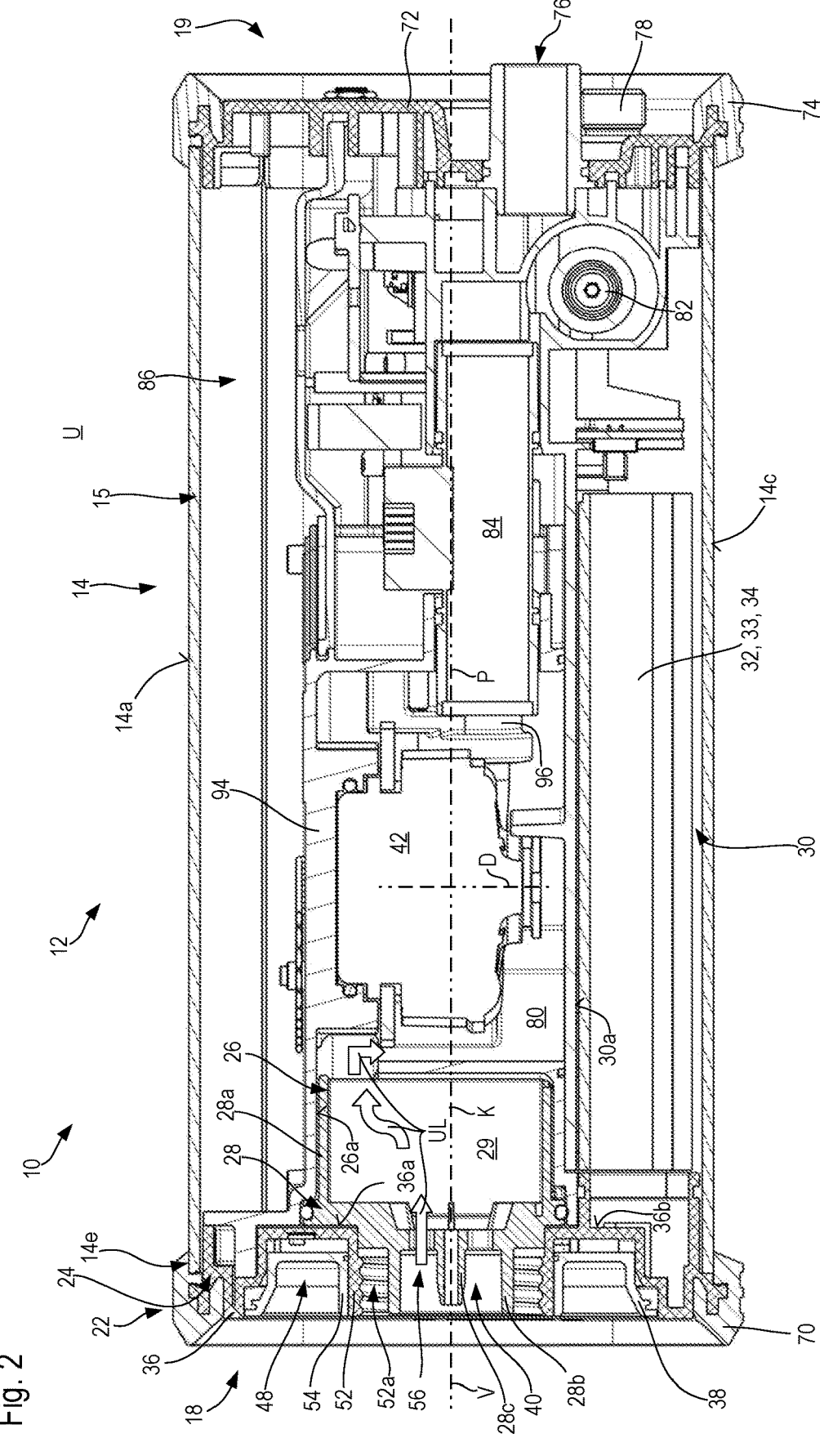

At the longitudinal end 14ƒ of the lateral surface 14 opposite the appliance lid 22 there is likewise arranged an appliance lid 72 (see FIG. 2). In contrast to the appliance lid 22, however, the appliance lid 72 is preferably not removable from the lateral surface 14 of the housing 12. In order to also protect the longitudinal end of the appliance lid 72 from axial and radial impact stresses, at this longitudinal end too there is provided an elastomer ring 74 encircling the prism axis P completely in a closed manner in the circumferential direction, which covers both part of the lateral surface 14 and part of the end face 19. The end face 19 is opposite the end face 18.

To simplify fabrication, the elastomer rings 68, 70, and 74 are preferably made from the same soft elastic material.

FIG. 2 shows a longitudinal section through the emergency ventilator 10 along a sectional plane which contains the prism axis P and proceeds in parallel to the planar area segments 14d and 14b.

As is discernible in the operational locking state of the emergency ventilator 10 shown in FIG. 2, the lid component 36 exhibits a lid-filter positioning section 36a which in the locking state is in abutting engagement with a section of the air filter cartridge 28, in particular with the cartridge main body 28a, thus contributing to a defined position of the air filter cartridge 28 and of the air filter 29 in the housing 12. The emergency ventilator 10 further exhibits a housing-filter positioning section 26a, for example in the shape of an inner wall of the filter accommodating compartment 26. Acting together, the lid-filter positioning section 36a and the housing-filter positioning section 26a define the operational position of the air filter cartridge 28 sufficiently accurately.

The lid component 36 likewise exhibits a lid-store positioning section 36b which in the depicted locking state is in abutting engagement with the energy store body 33, and acting together with a housing-store positioning section 30a, for instance an inner wall of the storage battery accommodating compartment 30, fixes the energy store body 33 sufficiently accurately in its operational position.

On the end face 19 in the housing-tight housing lid 72 there lies the respiratory gas output aperture 76 (see also FIG. 4), through which inspiratory respiratory gas conveyed by the fan 42 exits from the housing 12 towards a patient connected to the emergency ventilator 10.

Behind the sectional plane of FIG. 2, below the respiratory gas output aperture 76, there is provided, again in the housing-tight housing lid 72, a special gas coupling section 78, for instance a special gas connection nozzle, through which likewise a special gas different from ambient air can be introduced into the emergency ventilator 10. This special gas too, can for example be oxygen.

Consequently the emergency ventilator 10 permits the mixing of a respiratory gas from three different gases, namely from ambient air, from a first special gas introduced through the special gas coupling section 78, and from a second special gas introduced through the special gas auxiliary inlet 28c. If only one further special gas different from ambient air is needed for mixing the respiratory gas, it is preferably introduced via the special gas coupling section 78.

Ambient air UL aspirated through the ambient air aspiration aperture 40 enters, as depicted by the solid white arrows in FIG. 2, through the ambient air inlet aperture 56 into the cartridge main body 28a, passes through the air filter 29 and reaches a mixing chamber 80 in which the fan 42 with its aspiration aperture is arranged. The gas present in the mixing chamber 80 bathes a large part of the outer surface of the fan 42, thus contributing to its convective cooling.

A special gas introduced through the special gas coupling section 78, for example oxygen, can be suitably adjusted via the input/output device 58 in its mass flow through a variable proportional valve 82 and likewise via a special gas supply line 84 reaches the mixing chamber 80, where the ambient air UL and the special gas can already mix before entering the fan 42. Thus the fan 42 serves in the present case not only for conveying the respiratory gas but also for the most homogeneous mixing of the latter, such that the most homogeneous respiratory gas possible exits from the respiratory gas output aperture 76. The conveying line, which on the pressure side leads the respiratory gas from the fan 42 to the respiratory gas output aperture 76, lies in FIG. 2 behind the sectional plane of FIG. 2 and lies behind an electronics compartment 86 which is completely shielded physically against the special gas supply line 84 in order to exclude any ignition risk which a spark which could originate in the electronics accommodated in the electronics compartment 86 or even just sufficient heat in an environment of pure oxygen or highly elevated oxygen content could have. In the electronics compartment 86 there is accommodated a control device for controlling the operation of the emergency ventilator 10.

Figure 3:
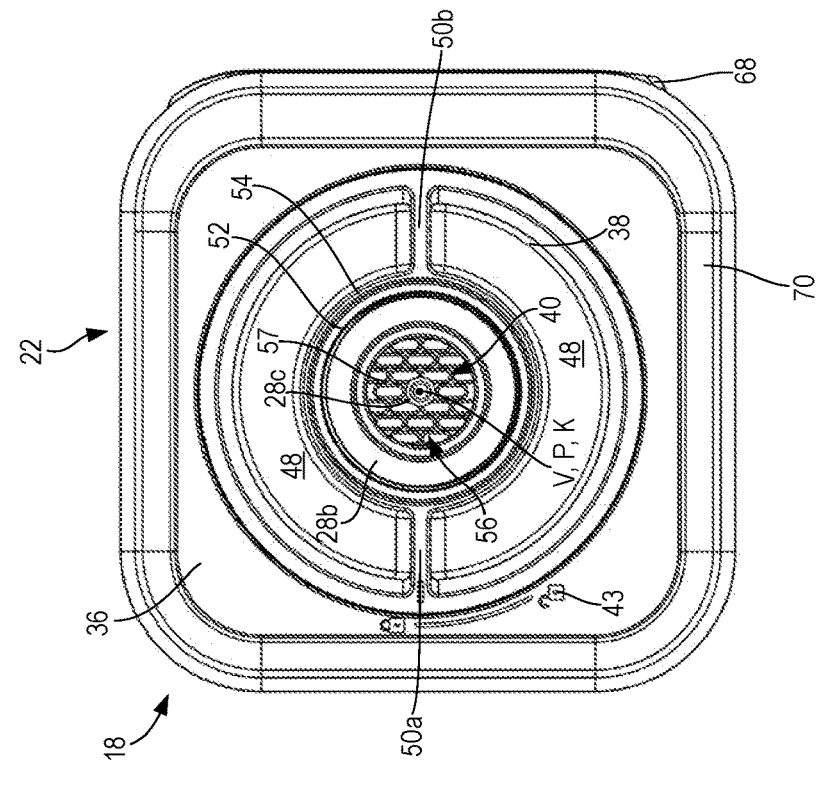

In FIG. 3 there is depicted a plan view of the end face 18 with the removable housing lid 22, i.e. with the direction of view along the coaxial axes latching axis V, prism axis P, and cartridge inlet axis K.

Figure 4:
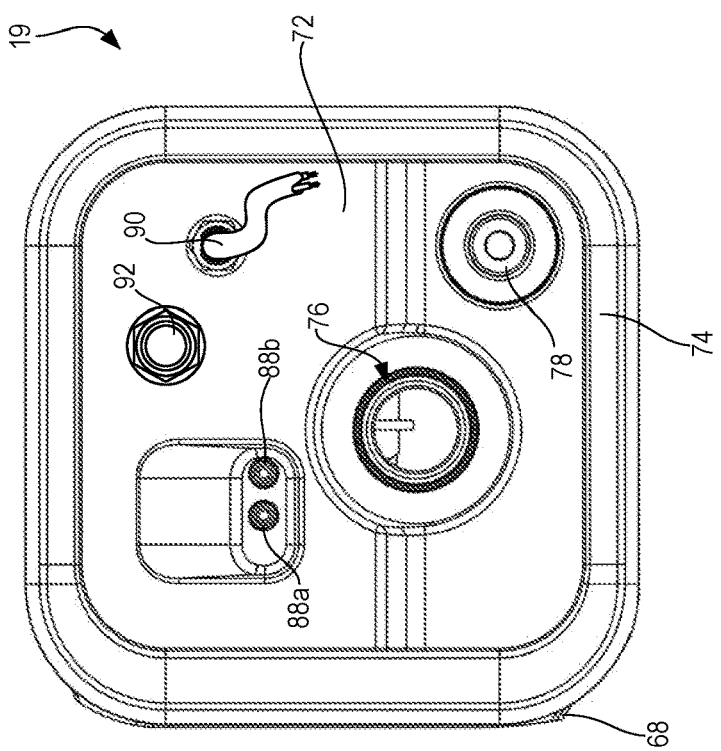

FIG. 4 shows a plan view of the end face 19 with housing-tight housing lid 72. The direction of view of FIG. 4 is opposite to that of FIG. 3.

Beyond the features already elucidated in connection with FIGS. 1 and 2, FIG. 4 shows connection nozzles 88a and 88b to which pressure acquisition hoses are connectable which at their other end lying distally from the connection nozzle 88a or 88b respectively are each connected with an inner region of a differential pressure flow sensor for measuring a proximal inspiratory and preferably also expiratory respiratory gas flow. The two inner regions are separated from one another in a manner known per se through a flow resistance, where the flow resistance is variable through the respiratory gas flow.

Given spatial availability of a power connection, the emergency ventilator 10 can be operated with energy from a public power supply grid via a power input 90. All electric functional units of the emergency ventilator 10 can then be supplied with grid voltage, normally with interposition of a power adaptor in the housing 12 which transforms to low voltage. The storage battery 32 can likewise be recharged. A socket 92 in the housing 12 is arranged for connecting an external sensor, in particular $CO_2$ sensor. Such a $CO_2$ sensor can for example be provided at a flow sensor coupled with the emergency ventilation device 10 and be coupled to a sensor arrangement.

Figure 5:
Figure 6:
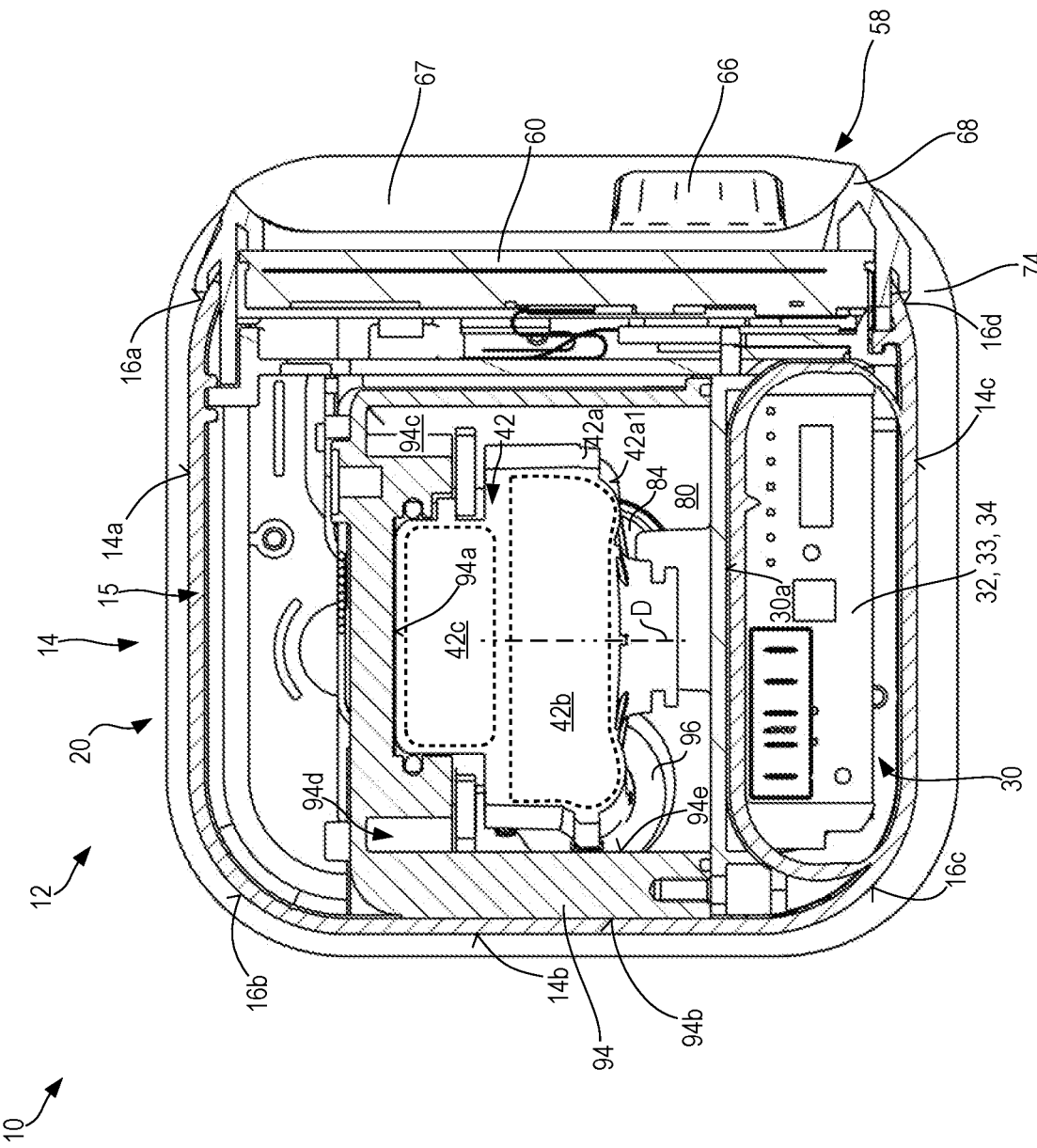
Figure 7:
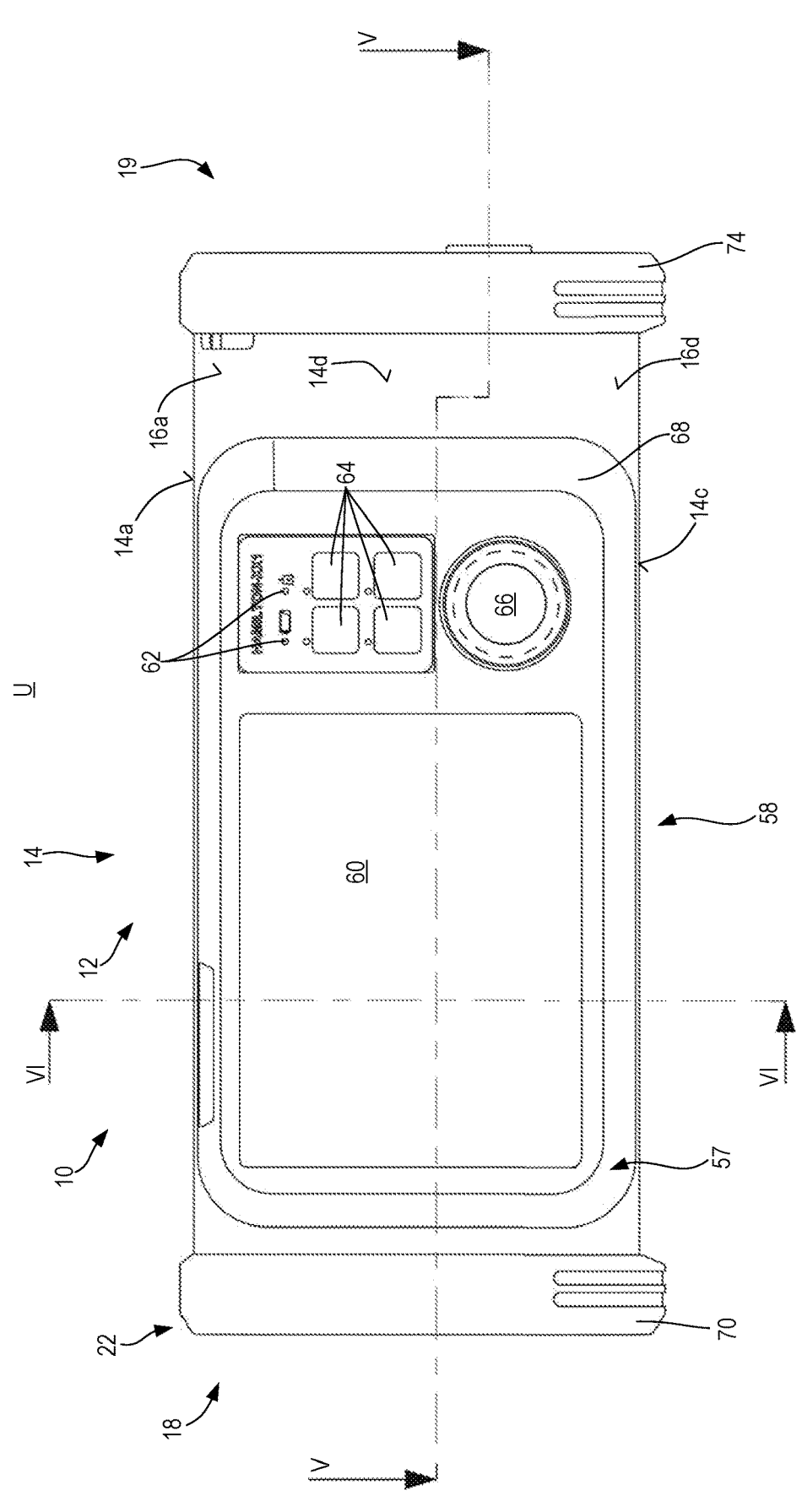

In the sectional views of FIGS. 2, 5, and 6, there is depicted in sectional view a heat-conducting body 94 to which the fan 42 is fastened.

As can be discerned in FIG. 6, in a lower section of the fan housing 42a there is accommodated an air conveyor 42b rotatably about a rotational axis D which is orthogonal to the planar area segment 14c and parallel to the drawing plane of FIGS. 2 and 6. An electric drive 42c located above the air conveyor 42b drives the air conveyor 42b which by way of example is configured as an impeller wheel to rotate. The lower section of the fan housing 42a can be configured as a separate conveyor housing part, on cost grounds for instance from a synthetic. To facilitate assembly, the conveyor housing part can itself in turn be configured in several parts.

A part of the fan housing 42a surrounding the drive 42c is attached in a recess at the heat-conducting body 94 bordered by a fan joint-face 94a with a small gap dimension of less than 1 mm, preferably of less than 0.3 mm, especially preferably gap-free, for example through gluing or soldering or welding or through fasteners such as bolts. This part of the fan housing 42a can be configured as a separate drive housing component, for better heat conduction for instance from an aluminum or metal alloy.

The fan housing 42a, preferably fabricated from aluminum by die casting or through machining from the solid, transfers heat from the fan 42 to the heat-conducting body 94. Since during the operation of the emergency ventilator 10 the drive 42c represents the most significant heat source inside the fan 42, the fan joint-face 94a preferably surrounds the region of the fan housing 42a which houses the drive 42c.

The heat-conducting body 94, likewise preferably fabricated from aluminum, exhibits at a distance from the fan joint-face 94a a housing joint-face 94b, with which the heat-conducting body 94 is connected with the housing 12 by full-face abutment against the inside of the housing section which exhibits the planar area segment 14b. The heat-conducting body 94 is preferably attached from outside with non-depicted bolts through clearance holes in the relevant housing section. The bolts penetrate through the clearance holes and are screwed into internal threads at the heat-conducting body 94.

In this way the housing joint-face 94b can be full-face connected gap-free with the housing section.

Alternatively to the depiction in FIGS. 2 and 6, there can be arranged between the fan joint-face 94a and the fan housing 42a and/or between the housing joint-face 94b and the housing 12 intermediate layers which enhance heat conduction, for example as a paste-like layer of a heat-conductive paste or on the other hand preferably as a solid layer in the shape of a heat-conductive mat.

Heat transferred by the fan 42 to the heat-conducting body 94 follows the temperature gradient which during operation develops at the planar area segment 14b, where normally at the contact surface to the external environment U there is present the lowest temperature in the path from the fan 42 via the heat-conducting body 94 up to the housing 12. At the area segment 14b, the heat from the heat-conducting body 94 transferred by the fan 42 to the housing 12 is given off to the external environment U through convection and radiation. A convective flow can naturally develop due to the temperature difference between the area segment 14b and the external environment U and will be the more pronounced, the greater the temperature difference between the area segment 14b and the external temperature U. Since the tubular housing component 15 exhibiting the lateral surface 14 is preferably made from the good heat-conducting material aluminum, the housing component 15 conducts heat from the area segment 14b also to neighboring area segments 14a, 16b, 16c, 14c, etc, such that such area segments can also contribute to the dissipation of heat to the external environment U which are not directly in touching contact with the heat-conducting body 94.

The housing joint-face 94b is more than twice as large as the fan joint-face 94a.

As can be discerned in FIG. 6, a large part of the outer surface 42a1 of the fan housing 42a protrudes into the mixing chamber 80, where the protruding part of the outer surface 42a1 can be bathed by respiratory gas in the mixing chamber 80. Thus the respiratory gas conveyed by the fan 42 too, can contribute to the convective cooling of the fan 42 and of the emergency ventilator 10 overall. The outer surface 42a1 completely surrounds the rotational axis D of the air conveyor 42b in the circumferential direction.

The cooling effect of the respiratory gas and of the heat-conducting body 94 is preferably so good that the emergency ventilator 10 does not exhibit a dedicated cooling fan, such that preferably the fan 42 is the only fan in the emergency ventilator 10 for conveying respiratory gas.

In FIG. 5 there is discernible a respiratory gas duct 96 as output duct of the fan 42. On the pressure side of the fan 42, the fan 42 conveys respiratory gas through the respiratory gas duct 96 in the direction towards the respiratory gas output aperture 76. The respiratory gas duct 96 proceeds in the depicted embodiment example in a space-saving manner in parallel to the special gas supply line 84.

In the heat-conducting body 94 there can be configured channels 94c and 94d which increase the surface of the heat-conducting body 94, which, driven by the fan 42, at least section-wise can have flowing through them respiratory gas in the mixing chamber 80 and thus additionally transport heat convectively away from the heat-conducting body 94. This additionally increases the cooling effect of the respiratory gas and of the heat-conducting body 94.

A surface 94e of the heat-conducting body borders the mixing chamber 80 and can be bathed by respiratory gas.

As can be discerned in an overall view foremost of FIGS. 5 and 6, the integral heat-conducting body 94 surrounds the mixing chamber 80 on five sides. In the mixing chamber 80 there are arranged the air conveyor 42b and the part of the fan housing 42a which surrounds the air conveyor 42b. The part of the fan 42 protruding into the mixing chamber 80 is arranged on all sides at a distance from the heat-conducting body 94, in order to achieve the largest possible area which can give off heat to the respiratory gas in the mixing chamber 80.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. An emergency ventilator for emergency medicine artificial respiration of patients, comprising:

a housing with an ambient air aspiration aperture and a respiratory gas output aperture, a fan which is configured and arranged in the housing in order to convey ambient air from the ambient air aspiration aperture to the respiratory gas output aperture, an air filter which is configured for cleaning aspirated ambient air and is arranged in the housing in a flow path of the ambient air downstream of the ambient air aspiration aperture, and an energy store for supplying the fan with energy for its operation, where the air filter is accessible through a first housing aperture which is closed by means of a first housing lid but is openable and in normal operation is accommodated in the housing in a replaceable manner, where the energy store is accessible through a second housing aperture which is closed by means of a second housing lid but is openable and in normal operation is accommodated in the housing in a replaceable manner, and where the first and second housing apertures are a common housing aperture and the first and second housing lid are a common housing lid such that the air filter and the energy store are thus accessible through the common housing aperture, where the common housing aperture can thus be closed and opened selectively through the common housing lid.

2. The emergency ventilator according to claim 1, wherein the common housing lid exhibits a lid component which in a locking state of the emergency ventilator, in which the common housing lid closes the common housing aperture, is immoveable relative to the remaining housing and a latching component which is moveable relative to the remaining housing, where the latching component is moveable between a latching position in which a latching formation of the latching component, through positive-locking engagement with a housing-tight latching counter-formation on the remaining ventilator, latches the common housing lid against removal from the common housing aperture, and a releasing position in which the latching component allows removal of the common housing lid from the common housing aperture.

3. The emergency ventilator according to claim 2, wherein the latching component is mounted on the lid component rotatably about a latching axis relative to the lid component.

4. The emergency ventilator according to claim 1, wherein the common housing lid exhibits the ambient air aspiration aperture.

5. The emergency ventilator according to claim 4, wherein the common housing lid exhibits a lid component which in a locking state of the emergency ventilator, in which the common housing lid closes the common housing aperture, is immoveable relative to the remaining housing and a latching component which is moveable relative to the remaining housing, where the latching component is moveable between a latching position in which a latching formation of the latching component, through positive-locking engagement with a housing-tight latching counter-formation on the remaining ventilator, latches the common housing lid against removal from the common housing aperture, and a releasing position in which the latching component allows removal of the common housing lid from the common housing aperture, the ambient air aspiration aperture penetrates through the latching component.

6. The emergency ventilator according to claim 5, wherein the latching component is mounted on the lid component rotatably about a latching axis relative to the lid component.

7. The emergency ventilator according to claim 5, wherein the latching component is mounted on the lid component rotatably about a latching axis relative to the lid component, the latching axis penetrates through the ambient air aspiration aperture.

8. The emergency ventilator according to claim 7, wherein the lid component exhibits a mounting section surrounding the ambient air aspiration aperture which is coaxial to the latching axis and which is surrounded by a mounting counter-section of the latching component which extends along the latching axis and is coaxial to the latching axis.

9. The emergency ventilator according to claim 8, wherein the mounting section exhibits an attachment formation, on its relative to the latching axis, radial inner side which faces away from the mounting counter-section.

10. The emergency ventilator according to claim 1, wherein the common housing lid exhibits a lid-filter positioning section which in a locking state faces towards the interior of the housing and which in the locking state with the emergency ventilator in a ready-to-operate state, acting together with at least one housing-tight housing-filter positioning section, secures a filter cartridge having the filter for filtering ambient air in its operational position, and/or the common housing lid exhibits a lid-store positioning section which in the locking state faces towards the interior of the housing and which in the locking state with the emergency ventilator in the ready-to-operate state, acting together with at least one housing-tight housing-store positioning section, secures an energy store body of the energy store in its operational position.

11. The emergency ventilator according to claim 10, wherein the filter cartridge exhibits an ambient air inlet aperture which can be reached through the ambient air aspiration aperture and a special gas connector formation for connecting a special gas supply.

12. The emergency ventilator according to claim 10, wherein the ambient air inlet aperture and the special gas connector formation are arranged coaxially to one another.

13. The emergency ventilator according to claim 10, wherein the ambient air inlet aperture and the special gas connector formation are arranged coaxially to one another, wherein in the operational locking state are also arranged coaxially to the latching axis.

14. The emergency ventilator according to claim 1, wherein the housing exhibits a prismatic and/or cylindrical basic form, where the common housing lid forms an end face of the prismatic and/or cylindrical housing.

15. The emergency ventilator according to claim 14, wherein all connector formations and/or apertures which introduce a gas into the housing and channel gas out of the housing are arranged at one of the end faces of the prismatic and/or cylindrical housing.

16. The emergency ventilator according to claim 15, wherein the prismatic and/or cylindrical housing exhibits in the region of its lateral surface an input/output device with a display device and at least one switching device.

17. The emergency ventilator according to claim 14, wherein the prismatic and/or cylindrical housing exhibits in the region of its lateral surface an input/output device with a display device and at least one switching device.

18. The emergency ventilator according to claim 1, wherein the common housing lid exhibits on its outer surface at least one shock-absorbing element.

* * * * *